United States Patent [19]

Hellstrom et al.

[11] Patent Number: 5,084,560
[45] Date of Patent: Jan. 28, 1992

[54] IMMUNOCONJUGATES AND METHODS FOR THEIR USE IN TUMOR THERAPY

[75] Inventors: Karl E. Hellstrom; Ingegerd E. Hellestrom; Efraim Lavie, all of Seattle, Wash.

[73] Assignee: Oncogen, Seattle, Wash.

[21] Appl. No.: 564,387

[22] Filed: Aug. 7, 1990

Related U.S. Application Data

[60] Division of Ser. No. 47,161, May 12, 1987, Pat. No. 4,997,913, which is a continuation-in-part of Ser. No. 880,674, Jun. 30, 1986, abandoned.

[51] Int. Cl.[5] ............... C07K 17/02; A61K 39/44
[52] U.S. Cl. ..................... 530/390; 530/391; 424/85.91
[58] Field of Search ............ 530/390, 391; 424/85.91

[56] References Cited

U.S. PATENT DOCUMENTS 4,631,190 12/1986 Shen et al. ............ 424/85.8

FOREIGN PATENT DOCUMENTS 1079268 6/1980 Canada .

OTHER PUBLICATIONS

Blair et al (1983) J. Immunol. Methods 59: 129–143.
Gallego et al. (1984) Int. J. Cancer 33:737–744.
Jung et al. (1981) Biochem. Biophys. Res. Commun. 101(2):599–606.

Primary Examiner—Jeffrey E. Russel
Assistant Examiner—Kay Kim
Attorney, Agent, or Firm—SaraLynn Mandel

[57] ABSTRACT

Novel pH-sensitive immunoconjugates which dissociate in low-pH tumor tissue, comprising a chemotherapeutic agent and an antibody reactive with a tumor-associated antigen are described. The chemotherapeutic agent is coupled to the antibody by a link which is unstable in low pH. The link may comprise a spacer consisting of a polyamino acid. Representative antibodies for use in these immunoconjugates include monoclonal antibodies which are not internalized by tumor cells.

10 Claims, 15 Drawing Sheets

IMMUNOCONJUGATES AND METHODS FOR THEIR USE IN TUMOR THERAPY

CROSS REFERENCE TO RELATED APPLICATION

This is a divisional of U.S. patent application Ser. No. 047,161, filed May 12, 1987, now U.S. Pat. No. 4,997,913 issued Mar. 5, 1991, which is a continuation-in-part of U.S. patent application Ser. No. 880,674, filed June 30, 1986 now abandoned.

FIELD OF THE INVENTION

The present invention relates to the production of novel immunoconjugates unstable at low pH, in particular to such immunoconjugates containing chemotherapeutic agents and to methods of using such immunoconjugates in chemotherapy.

BACKGROUND OF THE INVENTION

Although various chemotherapeutic drugs have been found effective against certain tumors and even curative against some (Pardee Devita and Hellman, eds., in *Cancer, Principles and Practice of Oncology*, Lippincott & Co. (1982)), there is a great need for therapeutic agents which kill cancer cells more efficiently and more selectively. An attractive approach towards meeting this need is to use antibodies to prepare antibody-drug complexes or "immunoconjugates" that direct or "target" anti-cancer agents to tumors. Antibodies are known in the art which recognize antigens expressed on cancer cells, for example the antibody 96.5 which reacts with the p97 antigen of human melanomas (Brown et al., *J. Immunol.*, 127 p. 539 (1981)). Several immunoconjugates of this type have been shown to be selectively cytotoxic to antigen-positive tumor cells in vitro, to localize in tumors in vivo, and to have anti-tumor activity in mice that is greater than that of the drug or antibody alone (Rowland et al., *Cancer Immunol. Immunotherapy*, 19, pp. 1 (1985)). While the ability of such immunoconjugates to cure human tumors remains to be demonstrated, improvements in tumor targeting have been the focus of recent research efforts.

For a chemotherapeutic agent to be able to exert an effect on tumors, it must be taken up by the tumor cells, since very few, if any, cancer drugs are otherwise cytotoxic. The immunoconjugates must, therefore, be directed to the cancer cells, for example by antibody recognition of tumor-associated antigens, and either be taken up by the cancer cells (with active drug being released inside the cells), or the active drug must be released in the close vicinity of the cancer cells, and internalized in the same way as when the drug is used conventionally. The second alternative has several advantages. First, while anticancer drugs can be taken up by most cells, the internalization of immunoconjugates depends on both the antigenic target of the respective antibody and the cell in which the antigen is expressed. Antibodies to antigens that undergo modulation, i.e., those antibodies that are internalized in the form of an antigen-antibody complex (Old et al., *Proc. Soc. Exp. Biol. Med.*, 124, p. 63 (1967)), are the ones most easily used for drug targeting (Jansen et al., *Immunol. Rev.*, 62, p. 185 (1982)). Second, there is heterogeneity in the expression by cells of most tumor antigens so that cells which do not express a given antigen, i.e., are antigen-negative, frequently occur within a tumor (Yeh et al., *J. Immunol.*, 126, p. 1312 (1981); Albino et al., *J. Exp. Med.*, 154, p. 1764 (1981)). Although the difficulty of accumulating effective levels of chemotherapeutic agents within a tumor as a result of tumor cell heterogeneity can be decreased by combining antibodies to different antigens expressed by the same tumor cells and forming immunoconjugates, it could be further minimized if a therapeutic approach was developed in which the presence of some minimal amount of cells possessing the given antigen within a tumor would be sufficient to allow localization of effective amounts of immunoconjugates. Third, there are some tumor antigens, mucins, for example, which are present in larger amounts outside of the cells than at the cell membrane, (Rittenhouse et al., *Laboratory Medicine*, 16, p. 556 (1985)) suggesting the potential for targeting tumor regions.

The acidity (pH) of tumor tissues appears to be lower than that of normal tissues. Studies conducted more than half a century ago showed that malignant tumors metabolize carbohydrates mainly by anaerobic glycolysis, even under aerobic conditions (Warburg et al., *Biochem. F.*, 152, p. 309 (1924)). The oxidation of glucose stops at the stage of glucose oxidation to pyrivic acid, followed by reduction to lactic acid (Boxer and Devlin, *Science*, 134, p. 1495 (1961)). Most of this lactic acid is either removed or buffered by surrounding extracellular fluid, but some of it accumulates extracellularly. This results in a lower pH within the tumor than in normal tissues. Elevation of the blood-sugar by intravenous infusion of glucose should accelerate anaerobic metabolism resulting in even more lactic acid in the tumor, and this should further increase the pH difference between tumors and normal tissues.

Following Warburg's studies, there have been several reports of lower pH in tumors of both experimental animals, (Voegtlin et al., *Nat'l. Inst. Hlth. Bull.*, 164, p. 1 (1935); Kahler and Robertson, *J. Nat. Cancer Inst.*, 3, p. 495 (1943); and human patients, Naeslund, *Acta Soc. Med. Upsal.*, 60, p. 150 (1955); Pampus, *Acta Neurochir.*, 11, p. 305 (1963)).

Meyer et al., in *Cancer Res.*, 8, p. 513 (1948) reported that the pH of malignant human tumors is lower than in normal tissues. In twelve out of fourteen cases, where both normal and neoplastic tissues from the same patients could be studied in vivo, there was a difference in pH which averaged 0.49 and ranged from 0.17 to 1.15.

Ashby, (*Lancet*, Aug. 6, p. 312 (1966)), found that the mean pH of malignant tumors from nine patients was 6.8 (ranging between 6.6 and 6.9). Raising of the blood sugar by intravenous infusion of dextrose further decreased the tumor pH to a mean of 6.5 (range 6.3–6.8).

Van Den Berg et al., *Eur. J. Cancer Clin. Oncol.*, 18, p. 457 (1982), showed that the pH of twenty-two human mammary carcinomas was 7.29 ($\pm 0.05$, SEM), as compared to 7.63 ($\pm 0.03$, SEM) in human subcutis, and observed similar differences in rat tumors. The differences between pH in tumors and normal tissues were highly statistically significant, although they were lower than those reported in the studies discussed above.

Thistlethwaite et al., *Int. J. Radiation Oncology Biol. Phys.*, 11, p. 1647 (1985), showed, likewise, that the pH of human tumors as measured by readings on fourteen tumors was below the physiological level with an average of $6.81 \pm 0.09$ (SEM). They speculated that the reported therapeutic effectiveness of hyperthermia depends on the lower extracellular pH of tumors as compared to normal tissues.

Trouet et al., U.S. Pat. No. 4,376,765, describe drug compounds composed of a protein macromolecule (carrier) linked via a peptide chain ("spacer arm") to an amino function of a drug. The carrier facilitates endocytic take-up by target cells so that the spacer arm may be cleaved within the cell. Recently, attention has been directed to developing antibody drug conjugates which release a drug within a tumor cell once the conjugate has crossed the cell membrane and encountered acidic pH (3.5-5.5) within the cell. U.S. Pat. No. 4,569,789 by Blattler et al., describes chemical formation of conjugates using crosslinking structures which can link amino-group substances such as chemotherapeutic drugs to the sulfhydryl portion of a compound such as an antibody reactive with tumor cell surface antigens capable of crossing the tumor cell membrane. One limitation of such a method of forming conjugates is that the antibody must contain a sulfhydryl group. This reduces the number of possible drug-antibody conjugates which may be formed using such procedures.

In spite of the published evidence that tumors have lower pH than normal tissues, and that acid-cleavable complexes may be formed between antibodies and drugs, this evidence has not yet resulted in the development of immunoconjugates which are composed of antibodies reactive with tumor associated antigens and chemotherapeutic agents, and which could be targeted to tumor tissues and are capable of selectively releasing the chemotherapeutic agents in the presence of the lower pH of cancer tissues for uptake by the tumor cells, but not at the pH of normal tissue.

SUMMARY OF THE INVENTION

In the present invention, pH sensitive immunoconjugates are provided for treating tumors in mammals by delivering a chemotherapeutic agent to tumor tissue. The immunoconjugates comprise an antibody reactive with a tumor-associated antigen coupled to a chemotherapeutic agent by a link which renders the conjugate unstable at low pH. In particular, the immunoconjugates comprise a monoclonal antibody which does not have to be internalized by tumor cells, and the chemotherapeutic agent is a compound such as an anthracycline compound effective in the treatment of tumors and possessing at least one free amino residue. A species of immunoconjugate showing particularly desirable properties for pH sensitivity in the range of pH of human tumor tissue, is that comprised of the L6 monoclonal antibody coupled by a poly-L-Lysine spacer to the drug Daunomycin.

BRIEF DESCRIPTION OF THE DRAWINGS

The present invention will be described in connection with the accompanying drawings in which.

Figure 1:
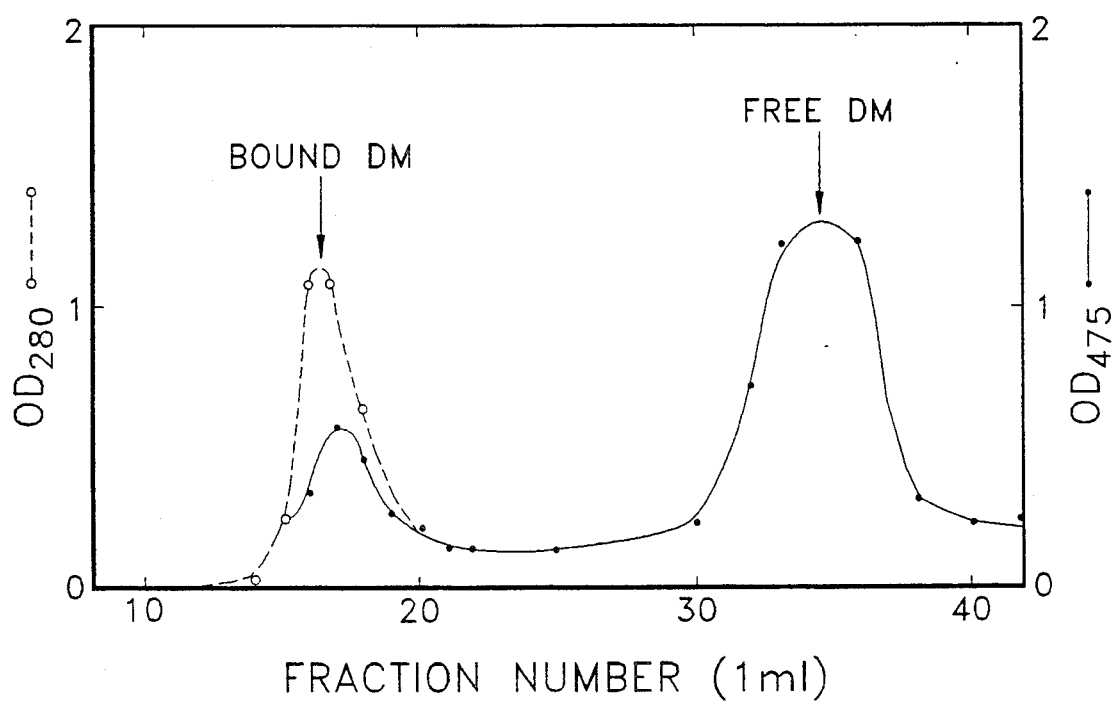
FIG. 1 is a graph depicting gel chromatographs of the antibody-Daunomycin immunoconjugate reaction mixture.

Accordingly, the present invention provides novel immunoconjugates composed of antibodies selectively reactive with tumor-associated antigens to target tumor tissues linked to chemotherapeutic agents. The immunoconjugates are unstable in low pH tumor tissues. The conjugates have a low toxicity at the pH of normal tissue, but when the conjugates localize in low pH tumor tissue as a result of recognition by the antibodies of the antigens associated with tumor cells because of the chemical instability of the conjugates, the chemotherapeutic agent is released and can be taken up by the tumor cells. Therefore, it is unnecessary for the entire conjugate to be internalized within the tumor cell, i.e., for the antibody to cross the cell membrane, for cell death to occur. In addition, those tumor cells which lack the target antigen can still be killed by the chemotherapeutic agent, provided a sufficient number of cells within the tumor express the antigen recognized by the antibody of the immunoconjugate. In addition, the invention includes methods for using these pH-sensitive immunoconjugates in chemotherapy, by introducing the conjugates into a patient to localize in low pH tumor tissue, where the chemotherapeutic is released and allowed to diffuse into the tumor cells. Thus, the expression of tumor-associated antigens in only a minimal number of the targeted tumor cells or tumor-associated tissue is required for tumor therapy, using the present invention. The examples set forth below demonstrate the ability of immunoconjugates prepared according to the invention, to localize in tumor tissue in an animal model.

To form the immunoconjugates of this invention, suitable antibodies must be selected or developed. The antibodies used for the conjugates are preferably monoclonal antibodies of either mouse or human origin, which are reactive with antigens that are expressed most strongly at the surface of tumor cells and/or in the close vicinity (i.e. outside the cell membrane) of tumor cells. Monoclonal antibodies may be produced using procedures such as those described by Kohler and Milstein in Nature, 256, p. 495, (1975). An example of one such monoclonal antibody, and the antibody preferred for use in this invention, is the L6 antibody (American Type Culture Collection "ATCC," No. HB8677), an IgG2a mouse immunoglobulin which is specific for a ganglioside antigen and which reacts with most human carcinomas. The ganglioside antigen (referred to as the "L6 antigen"), is expressed at the surface of cells of most human carcinomas, including non-small lung carcinomas, breast carcinomas, colon carcinomas and ovarian carcinomas. The L6 antibody and the L6 antigen are described in copending U.S. patent application, Ser. No. 684,759, and continuation-in-part application, Ser. No. 776,321 which were filed on Dec. 21, 1984, and Oct. 18, 1985, respectively, and assigned to the same assignee as the present invention, the disclosure of which is incorporated by reference herein. The L6 antigen does not modulate in the presence of L6 antibody (i.e., the antigen antibody complex is not internalized), indicating that the L6 antibody remains at the cell surface and is not taken up by tumor cells.

Additional monoclonal antibodies of mouse, rat, human or other origin can be generated to the L6 antigen, or other tumor-associated antigens. Chimeric antibodies, obtained by splicing together genes for the variable region of the antibody molecule (of mouse origin) and genes for the constant region (of human origin) as are exemplified by the work of Morrison et al., Proc. Natl. Acad. Sci., 81, p. 6851 (1984), and Takeda et al., Nature, 314, p. 452 (1985), may also be used. The immunoconjugates can also be made by using polyclonal sera which are prepared in various species, including rabbits and monkeys. Various fragments which are, for example, obtained by proteolytic digestion of antibody molecules, and include Fab, (Fab')$_2$, and Fc fragments can also be used. The present invention can equally well be carried out by using antibodies and fragments which are specific for antigens other than the L6 antigen, as long as the antibodies and fragments have a high affinity constant ($10^3$ M or better) and the antigen is either expressed in high levels at the tumor cell surface (at least 50,000 molecules per cell) or is present at relatively high levels in the immediate vicinity of the tumor cells.

Suitable chemotherapeutic agents for use in the present invention are those which have a cytotoxic and/or growth inhibitory effect on cancer cells. These include therapeutic agents of the type commonly used in the treatment of human cancer, including antineoplastic drugs such as the anthracycline compounds Daunomycin, Mitomycin C, Adriamycin, and antimetabolites such as the folic acid antagonist, for example, Methotrexate.

In the present invention, the immunoconjugates must be unstable at low pH to release the chemotherapeutic agent. This may be accomplished using several methods of chemical synthesis. In one approach, a pH-sensitive link such as aconitic anhydride, is attached to a chemotherapeutic agent and the carboxyl group (—COOH) of the agent is then coupled to the lysine group of the antibody. This approach is similar to the chemistry described by Shen and Ryser, Biochem. Biophys. Res. Comm., 102, p. 1048 (1981), incorporated by reference herein. Stable immunoconjugates between toxins and antibodies to certain lymphocyte populations for carrying the conjugate into the target cells, have been developed using such procedures; these immunotoxins have been found to be immuno-suppressive. Diener et al., Science, 231 p. 148 (1985).

The pH unstable immunoconjugates of the present invention may also be formed using an aconitic anhydride link to couple the chemotherapeutic agent to the antibody. These reactions are depicted below. In Step I of such a procedure, the labile gamma-carboxyl group of aconitic anhydride is reacted with a suitable chemotherapeutic agent, such as Daunomycin, containing at least one free amino group forming an intermediate compound (1). In the next step (II), this intermediate is reacted with an available antibody containing at least one lysine group, in the presence of carbodiimide reagent to form an immunoconjugate consisting of Daunomycin and antibody coupled by the link. This immunoconjugate (2) will dissociate in low pH medium such as tumor tissue as #2 shown in Step III.

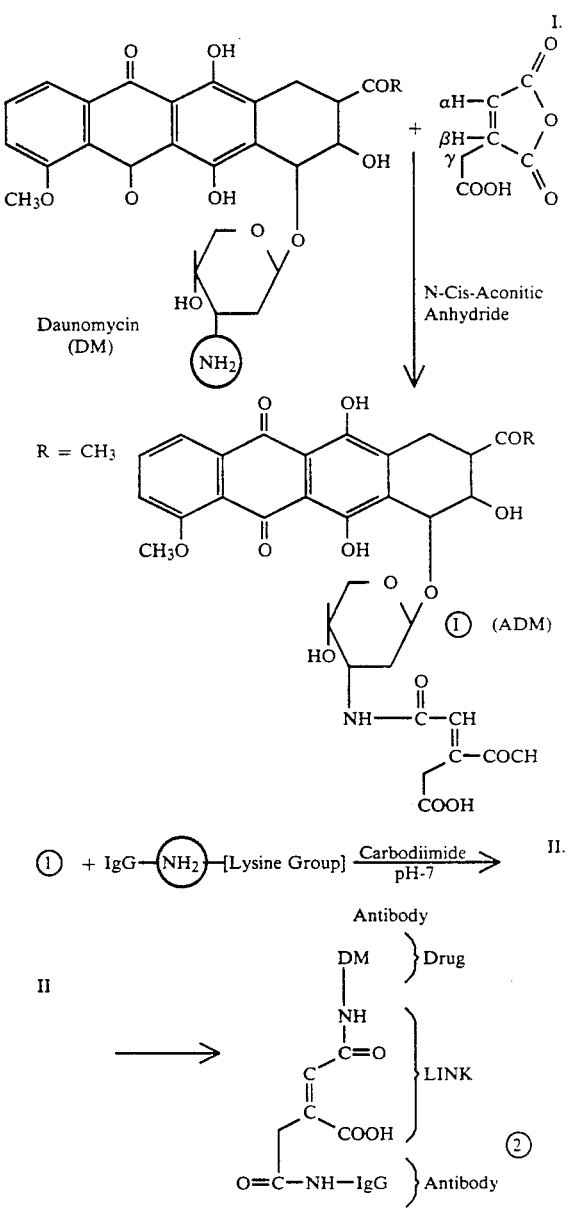

III At Low pH:

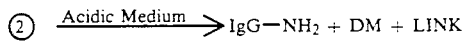

When the above chemistry is used to conjugate a monoclonal antibody such as L6 to a chemotherapeutic agent, for example, the anthracycline Daunomycin, relatively low yields of reaction may be obtained so that the amount of drug associated with antibody, which will be released, may be too low for optimum therapeutic effectiveness. In addition, the reactivity of the antibody may be affected by a polymerization reaction induced by the carbodiimide reagent used in the above reaction. Therefore, although the reaction may be used to form the immunoconjugates of this invention, it is preferable to improve the above reaction, for example, by using activating reagents, or by the use of spacer molecules.

Thus, to improve the reactions, a succinated intermediate of the anhydride modified chemotherapeutic agent and N-hydroxysuccinimide may be prepared using a carbodiimide reagent such as 1-ethyl-3-(3-dimethylaminopropyl) carbodiimide hydrochloride (EDC) to promote the activation of the carboxylic groups of the aconitic anhydride. This intermediate is then reacted with the amino group of an available lysine of the antibody to form an immunoconjugate with an amide bond. Such immunoconjugates are described, and the reactions shown, in Example II below.

Particularly useful immunoconjugates may be prepared which incorporate spacer molecules, preferably polyamino acids containing at least three amino acids such as poly-L-Lysine and poly-L-Glutamic acid and including protein molecules, for example, albumin. In a preferred conjugation process, the amino group of a lysine in a lysine-containing antibody is modified by thiolation, for example using S-acetylmercaptosuccinicanhydride (SACA) to provide free sulfhydryl groups (—SH). A spacer molecule, such as poly-L-Lysine is complexed with the anhydride modified chemotherapeutic agent prepared as described above, and the lysine group of the spacer molecule of the complex is then modified with a reagent such as maleimide reagent for example, sulfosuccinimidyl-4-(N-maleimidomethyl) cyclohexane-1-carboxylate. The thiolated antibody is then conjugated with the maleiimide-modified spacer molecule-chemotherapeutic agent complex to form an immunoconjugate capable of dissiciation at low pH.

Alternatively, in a series of reactions mediated by a reagent such as N-succinimidyl 3-(2-pyridyldithio) propionate (SPDP), lysine groups in a spacer molecule such as albumin are attached to the carboxyl group of the anhydride-modified chemotherapeutic agent (obtained as described above), and to the amino group of a lysine in the antibody. Immunoconjugates containing spacer molecules are set forth in Examples IV and V below.

Immunoconjugates having a spacer link may thus be prepared with several molecules of chemotherapeutic agent per antibody molecule (up to 50 molecules of agent per antibody molecule) which, in turn, enhances drug delivery to the tumor tissue, without significantly altering the reactivity of the antibody.

The level of conjugation using the above-described procedures may be further improved by modifying the pH of the reactions so that the pH is in the range of from 6.5 to 8.5, or by increasing the temperature during the reactions in the range of from 4° C. to 37° C. Additionally, the time of incubation may be modified to increase the amount of drug coupled to antibody from 3 up to 24 hours. Further, the ratio of chemotherapeutic agent introduced to the antibody in Step II of the reaction between antibody and the chemotherapeutic agent may be changed; final ratios of agent to antibody from 10 to 50 are preferred.

For the above approach of making the low pH unstable immunoconjugates using an aconitic anhydride link, the chemotherapeutic agent should possess at least one free amino group. Since the amino group is believed to be necessary for biological activity, the spacer is preferably completely hydrolyzed from the chemotherapeutic agent to free the amino group. Suitable chemotherapeutic agents which meet these requirements are the anthracycline compounds Daunomycin, Mitomycin C, Adriamycin, and methotrexate. These compounds also contain a quinone structure and an acyl (—COR) moiety, both of which are believed to be important for tumor cell destruction. A pH stable conjugate can be made, as a control, by using another spacer, maleic anhydride, in place of the aconitic anhydride.

A second approach for linking a chemotherapeutic agent to an antibody to form pH unstable immunoconjugates is based on chemical reactions using cyanogen bromide, similar to those described by Axen et al., in *Nature*, 214, p. 1302 (1967), incorporated by reference herein. Axen et al. describes coupling proteins to polysaccharide resins such as Sephadex. To carry out these reactions, the chemotherapeutic agent, for example, Daunomycin, is activated using cyanogen bromide (CNBR) at an alkaline pH (e.g., pH 11.0). The activated Daunomycin is then added to a solution of an appropriate antibody and a buffer solution, such as a sodium bicarbonate solution, to maintain an alkaline pH. The resulting conjugate is purified, for example, by column chromatography. The immunoreactivity of the conjugated antibody is tested by procedures such as immunohistology using the PAP technique (Garriques et al., *Inter. S. Cancer*, 29 p. 511 (1982)), or by radioactive binding assays. Immunoconjugates formed in this manner may then be tested in the pH range of tumor tissues, preferably in the range of from pH 5.6 to pH 6.7. These reactions may be summarized as follows. Briefly, the carbon of the cyanogen bromide is reacted with hydroxyl (—OH) groups of the chemotherapeutic agent to form a mixture of intermediates (1). The intermediates are reacted with the amino group of a lysine amino acid of the antibody to form a mixture of immunoconjugates (2), having an amino group of a lysine amino acid of the antibody coupled via a carboxyl link to hydroxyl groups of the chemotherapeutic agent.

These reactions are:

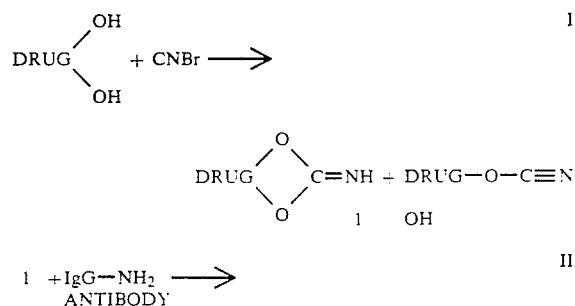

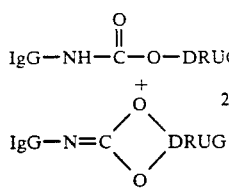

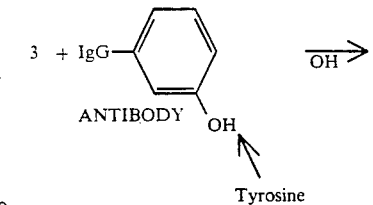

Since the immunoconjugates (2) are not stable at low pH, the conjugate dissociates in low pH medium into free drug and antibody as shown below.

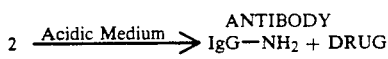

The chemotherapeutic agent should contain at least two hydroxyl groups, and the antibody should contain at least one lysine amino acid for these reactions.

A third approach for forming acid-cleavable bonds uses diazotization, following a method described by Cuatrecasas for forming conjugates, *J. Biol. Chem.*, 245, p. 3059 (1970), incorporated by reference herein, and consists of the following steps. The chemotherapeutic agent, for example, Daunomycin, is activated using a reagent such as P-nitro benzyl chloride in solution. After incubation, the nitro group is reduced, using a stannous chloride solution. The product of this reduction is then diazotized by adding HCl while cooling on ice. Sodium nitrite is added to induce diazotization. The activated Daunomycin is then conjugated with an available tyrosine amino acid of a suitable antibody using sodium bicarbonate to form a nitro-benzoyl link between the antibody and the drug. The pH is then adjusted, preferably to a pH of approximately 8.0. The conjugated antibody is then purified using column chromatography, and the immunoreactivity of the conjugated antibody is tested. These immunoconjugates are tested for release of the Daunomycin at pH in the range of 5.6 to 6.7. These reactions are represented as follows:

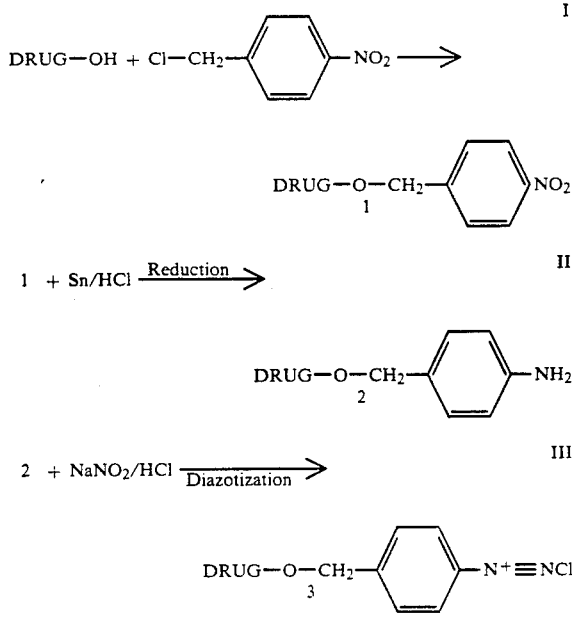

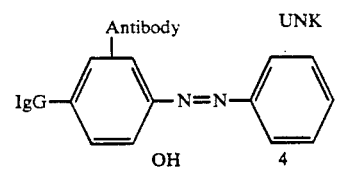

Since the immunoconjugate is unstable at low pH, the drug will be released into the tumor tissue by dissociation (Step V).

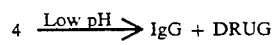

The chemotherapeutic agent employed in the above reactions (the third approach), should contain at least one hydroxyl (—OH) group, and preferably the antibody should contain at least one tyrosine amino acid in its structure.

The following examples are presented to illustrate the present invention and to assist one of ordinary skill in the art in making and using the same. The examples are not intended in any way to otherwise limit the scope of the disclosure or the protection granted by Letters Patent hereon.

EXAMPLE I pH of Tumor Tissue in Humans

To investigate the in vivo pH of several types of tumor tissues in humans, the following study was performed at the Virginia Mason Hospital in Seattle, Wash., in March of 1986.

Ten patients (8 females and 2 males; mean age 67.3 years) with different types of tumors were entered in an acute study during surgery. A flexible pH probe, diameter 1.2 mm (Microelectrode 20142, Microelectrodes, Inc., New Hampshire, U.S.A.) connected to a digital pH meter (Bechman Model 3500) was inserted into normal tissue and tumor tissue through a 14-gauge needle with the patient's index finger connected to a reference electrode (NMI-401, Microelectrodes, Inc.). The probe was calibrated before and after the procedure for each patient by use of commercially available buffers, pH 7, (Beckman) and pH 2 (Ricca Chemicals, Arlington, Tex.). The probe was sterilized with Turgicos solution (Johnson & Johnson, Arlington, Tex.). The pH values were recorded after stabilization, usually within 5-10 minutes in normal tissue, and the same procedure was repeated in tumor tissue. Two of the patients received 50 ml of a 50% glucose solution intraveneously ("i.v."). The glucose was given over a 30 min. period beginning one hour before surgery. The findings of this study are summarized in Table 1, which demonstrates a consistent, highly significant difference (0.8 pH units) between various tumors and normal tissue.

TABLE 1
pH Measurements in Tumors and Normal Tissues from Ten Patients

|  | Age | Sex | Diagnosis | Given i.v. glucose | A pH of normal issue | B pH of tumor tissue | Difference (A-B) |
|---|---|---|---|---|---|---|---|
| 1) | 76 | F | Cancer of the colon with mets | Yes | 7.2 Subc. | 5.9 | 1.3 |
| 2) | 57 | M | Undif. mesenchymal tumor | Yes | 7.4 Subc. | 6.6 | 0.8 |
| 3) | 80 | F | Rectal cancer | No | 6.9 Pararectal | 6.4 | 0.5 |
| 4) | 46 | F | Mammary cancer | No | 7.4 Subc. | 6.7 | 0.7 |
| 5) | 68 | F | Malignant melanoma | No | 6.9 Subc. | 6.0 | 0.9 |
| 6) | 48 | M | Lymphoma with axillary mets | No | 7.4 Subc. | 6.7 | 0.7 |
| 7) | 78 | F | Cancer of the cardia adenocarcinoma | No | 6.9 Subc. | 6.0 | 0.9 |
| 8) | 77 | F | Mammary cancer mets | No | 7.1 Subc. | 6.5 | 0.6 |
| 9) | 76 | F | Hypernephroma | No | 7.3 Subc. | 6.6 | 0.7 |
| 10) | 67 | F | Cancer of the esophagus | No | 7.3 Subc. | 6.2 | 1.1 |

Mean ± SEM = 7.2 ± 0.1 normal tissue.
Mean ± SEM = 6.4 + 0.1 tumor tissue.
mets = metastasis
Subc. = subcutaneous
P value = $1.9^{-06}$

EXAMPLE II

Daunomycin-Antibody Immunoconjugate

Preparation of Anhydride-Modified Daunomycin (ADM)

12 mg of Daunomycin ("DM") (Sigma Chemical Co., St. Louis, Mo.) were dissolved in ice-cold water, and a solution of 3 ml dioxane containing 12 mg of cis-aconitic anhydride was added drop-wise. The pH was adjusted to 9.0 by the addition of 0.5N NaOH. The mixture was stirred for fifteen minutes, after which the pH was decreased to 7 by adding 0.5M HCl. The solution ("ADM solution") was stirred for an additional hour. This derivative was designated "ADM".

Figure 3:
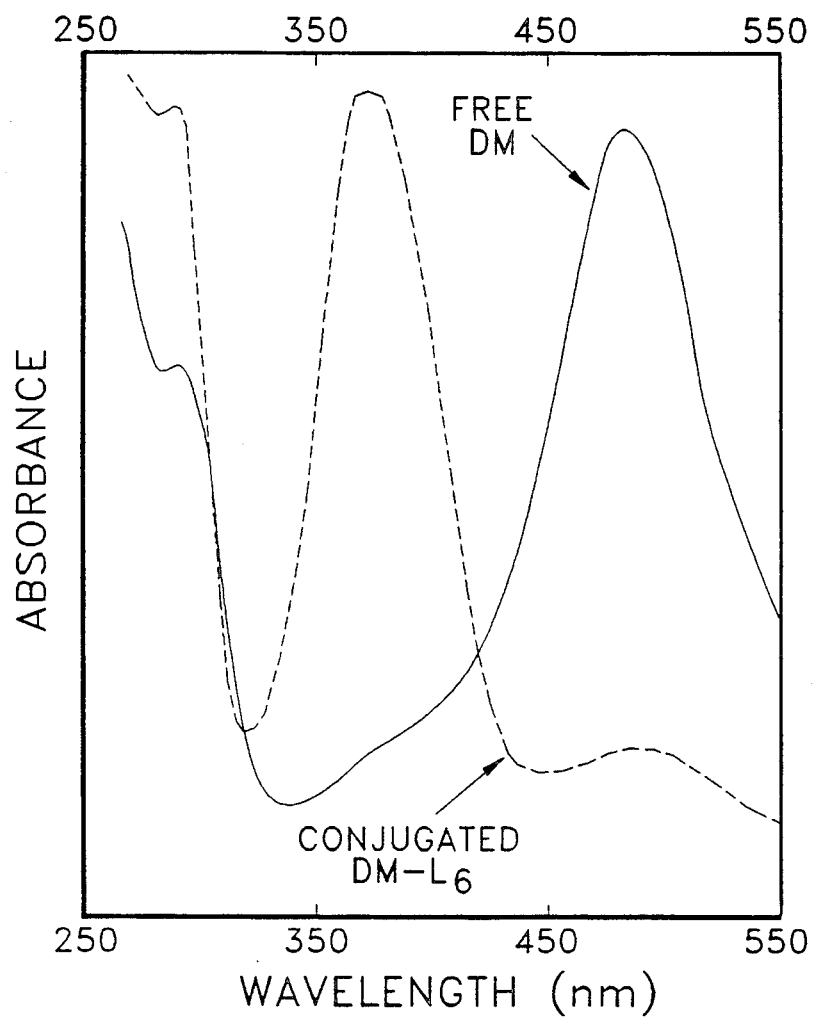
FIG. 3 depicts the absorption spectra of the free and conjugated forms of Daunomycin.

The proportion of free (unmodified) to modified DM ("ADM") was estimated using thin-layer chromatography on a mixture of acetone:chloroform:acetic acid (17:3:1). The "Rf" of free drug was approximately 0.1 and that of the spacer-DM (hereafter ADM) was approximately 0.5. Spectroscopy showed that both DM and ADM had absorbance peaks at 475 nm and at 280 nm. (FIG. 3).

Preparation of Antibody-Daunomycin Immunoconjugate

L6 antibody (ATCC No. HB8677), was dissolved in phosphate buffered saline (PBS), pH 7, and 0.6 ml of the ADM solution prepared as described above was added drop-wise to 10 mg of the L6 antibody in 0.8 ml of PBS. Subsequently, 10 mg of (1-ethyl-3)3-dimethylaminopropyl) carbodiimide hydrochloride (EDC) was added, and the mixture was kept at 4° C. and at a pH of 7.0 for 3 hours. The mixture was then loaded onto a Sephadex G-50 column (38×1.8 cm), and 1 ml fractions were collected. The antibody-drug conjugate exhibiting the yellow color of the drug, was eluted in fractions 16 and 17, and the free DM was eluted in fractions 35–42, as shown in FIG. 1. The yield of the conjugation reaction was 7-10%, and a ratio of 3:1 DM molecules per antibody molecule was obtained.

Figure 2:
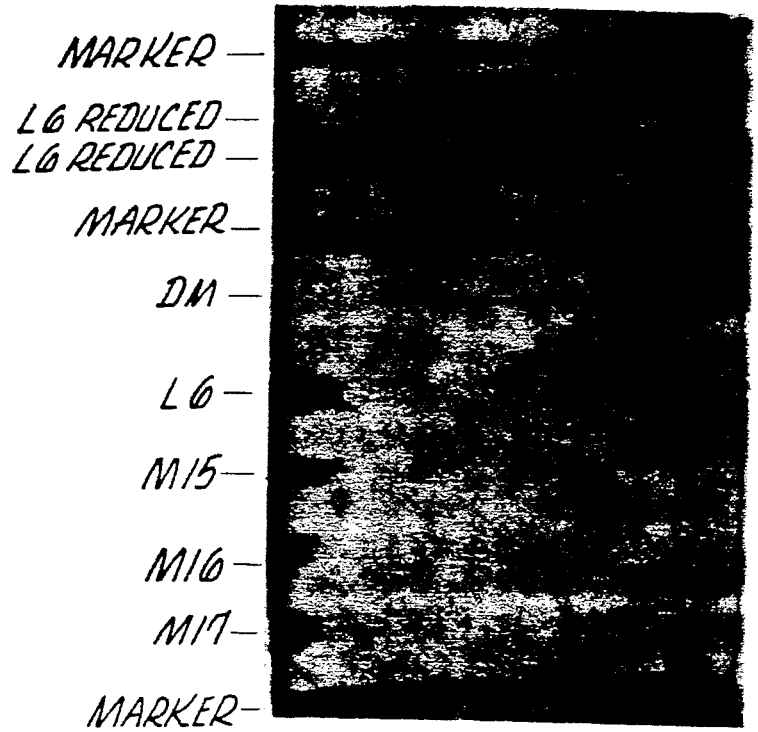
FIG. 2 is a photograph of an electrophoretic (SDS) gel of modified and unmodified antibody.

Tests by immunohistology, following the PAP procedures of Garrigues et al., supra, incorporated by reference herein, were performed to study the ability of the conjugate to bind to tumors expressing the L6 antigen. The tests showed that the immunoreactivity of the conjugate was preserved, although it was weaker than that of the native antibody. These tests were followed by cell binding assays using techniques described by Beaumier et al., J. Nuclear Med., 27 p.824 (1986). Approximately 80% of the original immunoreactivity was preserved. Gel-electrophoresis (7% SDS) showed only one band of the conjugated protein. This band was identical to that of unmodified IgG (MW, 150 k), FIG. 2, indicating that most of the conjugate remained in a monomeric state and did not polymerize.

An absorption spectrum of the purified product showed a new peak at 370 nm. (FIG. 3). This peak indicates that a convalent bond was formed in the conjugation between the DM and the L6 antibody.

Release of Daunomycin From the Immunoconjugate at Low pH in a Cell-Free Medium

Figure 4:
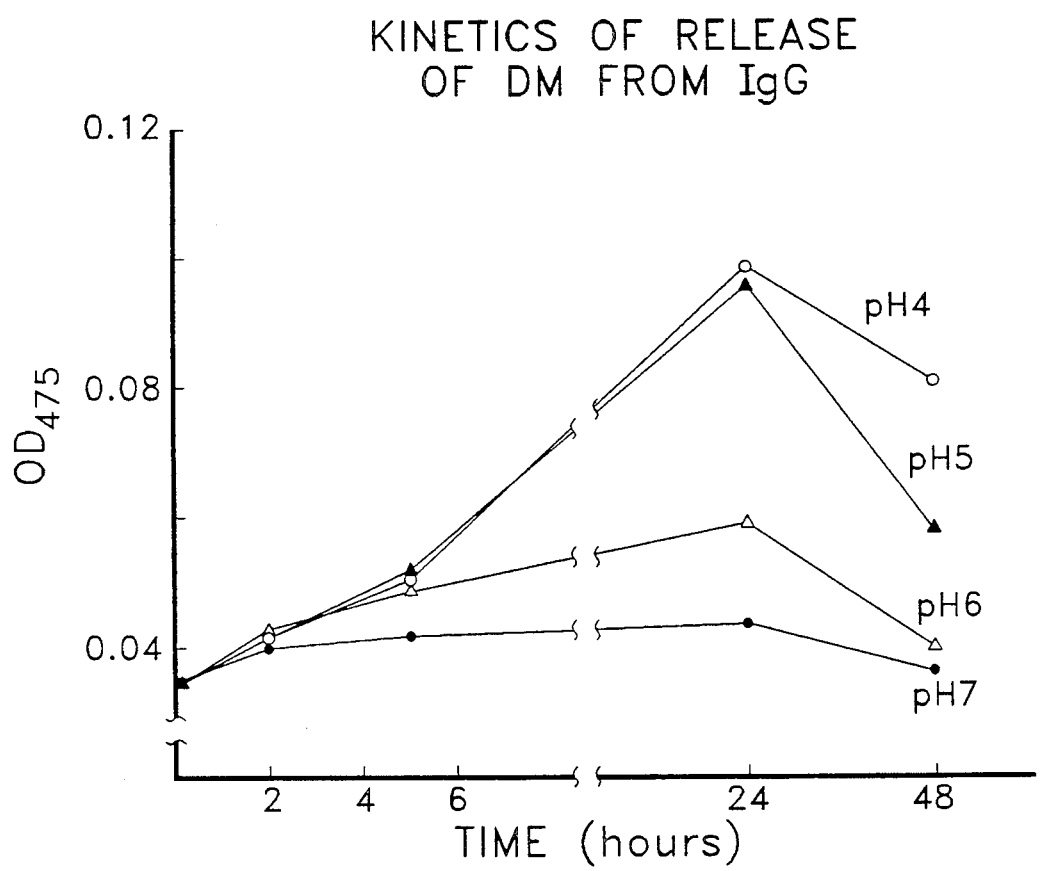
FIG. 4 illustrates the effects of changes in pH on the kinetics of release of Daunomycin conjugated to human IgG.

The purified immunoconjugate was mixed with citratephosphate buffers of four different pHs: pH 4, 5, 6 or 7, after which the mixtures were incubated at 37° C. and 1 ml aliquots removed at different time intervals. In order to separate DM which was released from the conjugate, conjugates were filtered through a Centricon-10 Filter (Amicon, Danvers, Mass.) which has a filtration cut-off at 10,000 daltons molecular weight, after which the absorbance of the supernatant was checked for presence of free DM (which absorbs at 475 nm). FIG. 4 depicts data obtained with a conjugate prepared by coupling DM to human IgG which serves as a readily available model for conjugation, rather than to the L6 antibody. FIG. 4 shows that after 24 hours of incubation at pH 4 or 5, between 30–40% of the DM has been released from the conjugate. At pH 6 approximately 15% of the DM was released. No significant release was noticed at a neutral pH.

Cytotoxicity of Daunomycin on Cultured Cell Lines

Figure 5:
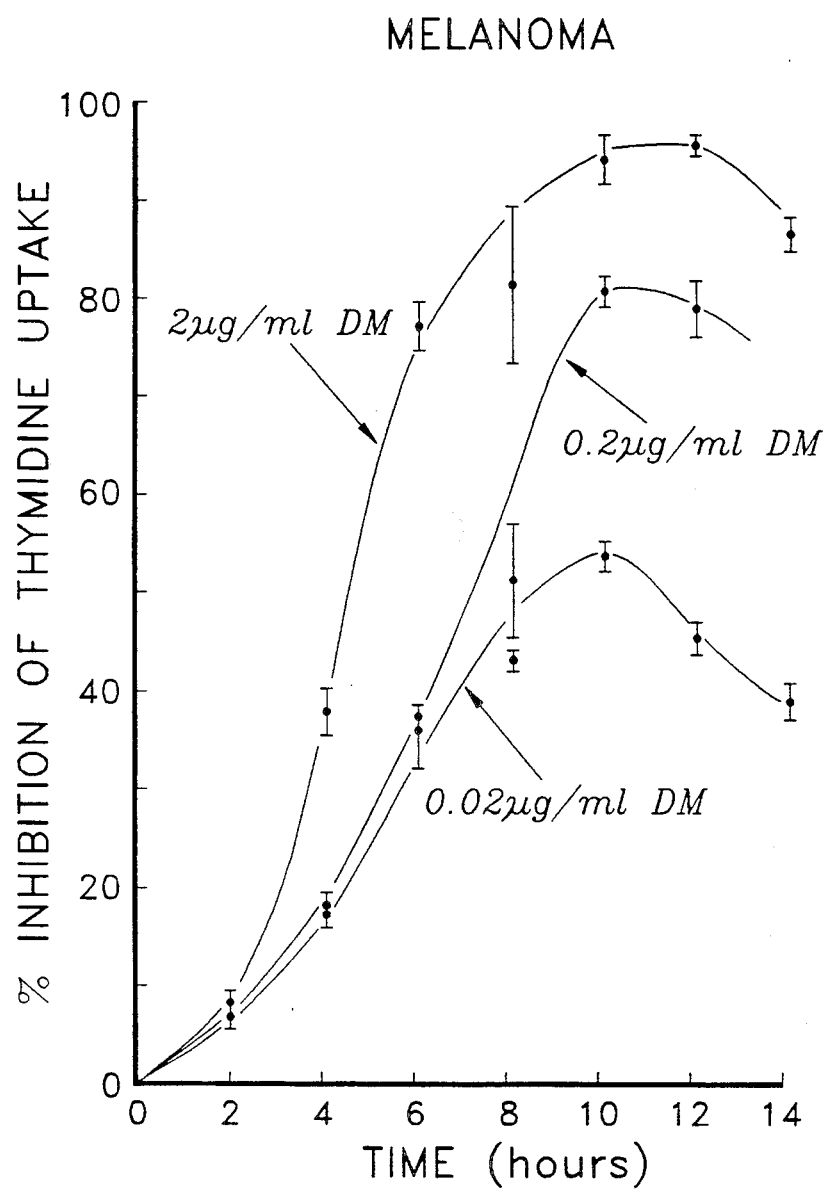
FIG. 5 is a graph of the toxicity to melanoma cells of various doses of free Daunomycin as measured by 3[H] thymidine uptake by cells over time.
Figure 6:
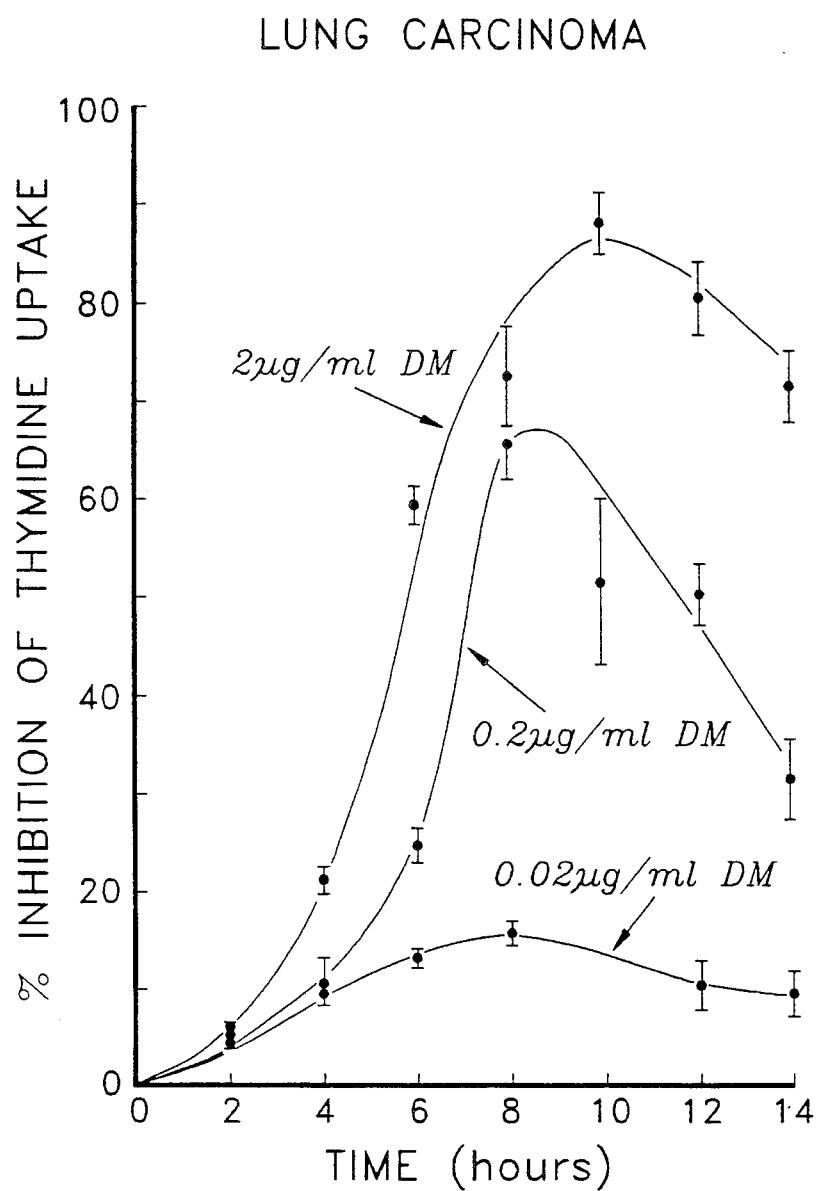
FIG. 6 is a graph of the toxicity to lung carcinoma cells of various doses of Daunomycin as measured by 3[H] thymidine uptake by cells over time.

The ability of DM to inhibit $^3$[H] thymidine uptake by cells from an explanted human lung carcinoma, 2981 (Oncogen, Seattle, Wash.), which can bind the L6 antibody, and by cells from melanoma M-2669 (Oncogen, Seattle, Wash.), which cannot, was measured. As shown in FIG. 5, free DM was very effective even at a low dose, less than 0.5 μg/ml. Cytotoxicity was observed after only 16 hours incubation with the drug, as illustrated in FIG. 6.

Binding of Antibody to Tumor Cells

Figure 7:
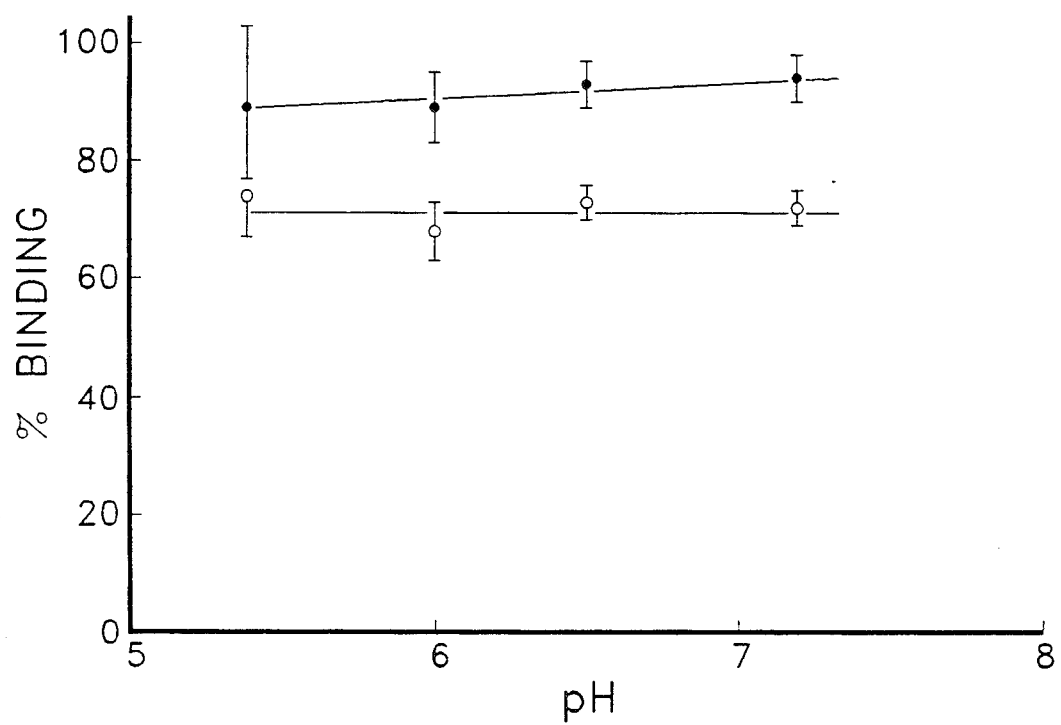
FIG. 7 is a graph of the binding of the L6 antibody to lung carcinoma cells, and of the 96.5 antibody to melanoma cells at different pH.

The antibody used to form the immunoconjugate herein, L6, as well as another antibody 96.5, demonstrate the ability to bind to tumor cells (lung carcinoma and melanoma) in the range of pH from 5 to 7. (FIG. 7). Thus, antibody binding is not likely to be inhibited by the pH found in tumor tissue. (Table 1).

EXAMPLE III

Amide-Linked Daunomycin-Antibody Immunoconjugate

Preparation of Succinated ADM

To maximize the amount of chemotherapeutic agent associated with the antibody of the immunoconjugates of this invention, ADM solution was prepared as described above in Example II. To 4 ml of ADM solution, 10 mg of N-hydroxysuccinimide (Fluka, Basel, Switzerland) and 5 mg of EDC was added. This mixture was stirred at room temperature for 24 hours (pH 5) to make the succinated product ("ADM-SUC").

Conjugation to Antibody 1.0 ml of ADM-SUC was added to 1 ml of L6 antibody (5 mg/ml in PBS buffer). The pH was adjusted to 8.5 with 1M NaOH. The mixture was incubated for 24 hours at 4° C., then purified using a G-50 sephadex column. The immunoconjugate was isolated as described in Example II, and contains an amide link between the antibody and the Daunomycin. The reactions may be depicted as follows:

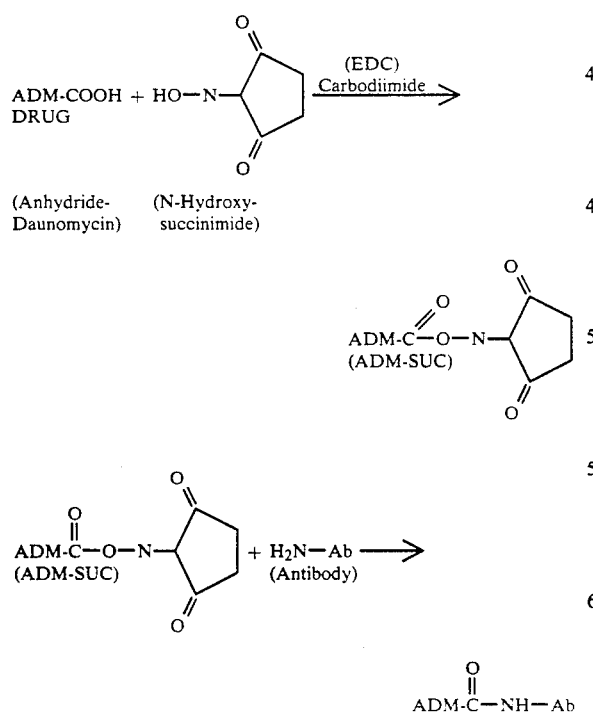

The conjugation yield was higher for the reactions in this example, and a DM to antibody ratio of 10:1 was obtained.

EXAMPLE IV

Daunomycin-Antibody Immunoconjugate Using Albumin Spacer

Modification of Antibody

To 1-ml of the antibody L6 (5 mg/ml) was added 63 μl of a solution of SPDP (7 mg/5 ml ethanol), and the mixture was incubated for 30 minutes at room temperature to modify a lysine amino acid of the antibody. The SPDP-modified antibody was then purified on a PD-10 (Pharmacia, Sweden) chromatography column, prewashed with a 0.1M sodium acetate solution (pH 4.5). The eluted peak was then reduced with 0.24 ml of dithiothreitol (DTT) (0.5M) for 10 minutes.

Attachment of Albumin to Daunomycin 1 ml of human serum albumin (HSA) was added to 0.65 ml of anhydride-modified Daunomycin (ADM) solution (prepared as described in Example II). 20 mg of EDC were added to the mixture to form a DM-HSA complex and incubated for 20 hours at 4° C. The complexed ADM-HSA was then purified on a G-50 sephadex column. The molar ratio of ADM to HSA was 20:1.

Modification of ADM-HSA

The ADM-HSA solution was incubated with 21 μl of SPDP solution (7 mg/5 ml of ethanol) for 30 minutes at room temperature to form SPDP modified (ADM-HSA) which was then purified on a PD-10 column.

Conjugation

The reduced, SPDP modified L6 antibody and the SPDP modified ADM-HSA were then mixed together to form an immunoconjugate of Daunomycin coupled to antibody by an albumin spacer. The ratio of DM to albumin was approximately 7:1. The reactions were:

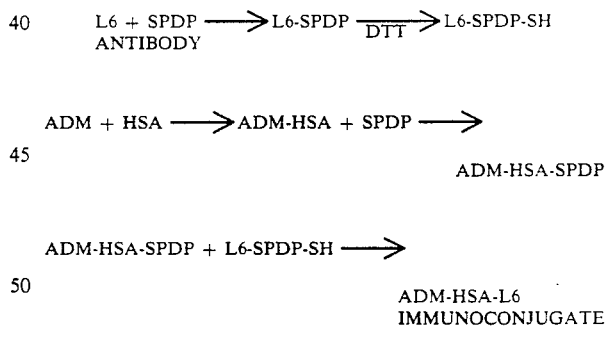

EXAMPLE V

Daunomycin-Antibody Immunoconjugate Using Poly-L-Lysine Spacer

Preparation of Anhydride-Modified Daunomycin (ADM)

Sixteen (16) mg of Daunomycin ("DM") (Sigma Chemical Co., St. Louis, Mo.) were dissolved in 1.5 ml of ice-cold water. 16 mg cis-aconitic anhydride was slowly added to the dissolved Daunomycin. The pH was adjusted to 9.0 by the addition of 0.5N NaOH. The mixture was stirred for 15 min, and the pH was then decreased to 3 by adding HCl. The solution was stirred in the cold (4° C.) for 15 min. The pellet was then isolated by centrifugation for 15 min at 4° C. at 3000 rpm.

The pellet was resuspended in 1 ml of PBS and the pH adjusted to approximately 8. This derivative was designated "ADM".

Attachment of Poly-L-Lysine to Daunomycin

To 10 mg of poly-L-lysine (PLS) (Sigma Chemical Co., St. Louis, Mo.), MW 60,000, 0.67 ml of ADM solution, pH 7, was added. Then 20 mg of EDC were added to the reaction mixture. The mixture was stirred for 24 hours at 4° C., then the modified PLS (ADM-PLS) was purified on a G-50 sephadex column, as described in Example III. More than 70% of the ADM became associated with the eluted PLS.

Preparation of Daunomycin-Poly-L-Lysine-Antibody Immunoconjugate

Thiolation of L6 Antibody (L6-SH)

10 mg of L6 antibody were dissolved in 1 ml of PBS. The pH was then adjusted to 6.5 with 1N HCl. 40 μl of S-acetylmercaptosuccinicanhydride solution (SACA) (stock: 12.6 mg reagent in 0.1 ml dried dimethyl formamide) was added to the antibody solution. The dimethyl formamide was freshly dried over molecular sieves (Aldrich Company, Milwaukee, Wis.). Thiolation was conducted for 30 min at 25° C. The following reagents were then added: 0.1 ml 0.1M Tris-HCl, pH 7, 10 μl 0.1M EDTA pH 7, and 0.1 ml 1M hydroxylamine, pH 7. The mixture was incubated for 5 min at 30° C. and was then loaded on a G-25 Sephadex column (25×1.8 cm). The column was prewashed with phosphate buffer 0.1M, pH 6, which contained 5 mM EDTA. The fractions of the modified antibody were collected, pooled and concentrated to a volume of 0.3 ml.

Maleimide reaction of PLS-ADM

To 1 ml of PLS-ADM complex (pH~7.2) 25 μl of sulfosuccinimidyl-4-(N-maleimidomethyl) cyclohexane-1-carboxylate solution (maleimide reagent, "ME") (17 mg maleimide reagent per 50 μl dried dimethylformamide) was added dropwise. The mixture was incubated for 30 min at 30° C. It was then loaded on a Sephadex G-25 column (12×1.8 cm) and eluted with PBS. Fractions containing modified (PLS-ADM-ME) were pooled and concentrated to a volume of 0.6 ml.

Linking of ADM-PLS to L6 antibody and purification of the conjugate

To 0.3 ml of modified L6 (L6-SH), 0.6 ml of modified PLS-ADM-ME were added dropwise. The pH was adjusted to 6.2. Nitrogen was then purged into the mixture for 3 min. The mixture was incubated for one hour at 30° C. in a sealed tube. 2 mg of 2-ethyl maleimide were then added to block excess -SH groups on the antibody. The reaction was continued for 20 min at 30° C. The L6-PLS-ADM conjugate was purified by precipitating with saturated (55%) ammonium sulfate solution (30 min at 4° C.). The sample was then spun down at 9000×g for 10 min at 4° C. and the pellet which formed contained the conjugate. The pellet was resuspended in 0.5 ml of PBS buffer. The pH was adjusted to 7.5. The molar ratio achieved by using this approach was between 18 and 25 molecules of Daunomycin for each antibody molecule. The purified conjugate was subsequently tested for binding to tumor cells and for cytotoxicity.

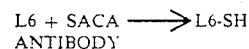

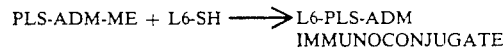

Binding of the L6-PLS-ADM immunoconjugate to a carcinoma cell line

Figure 8:
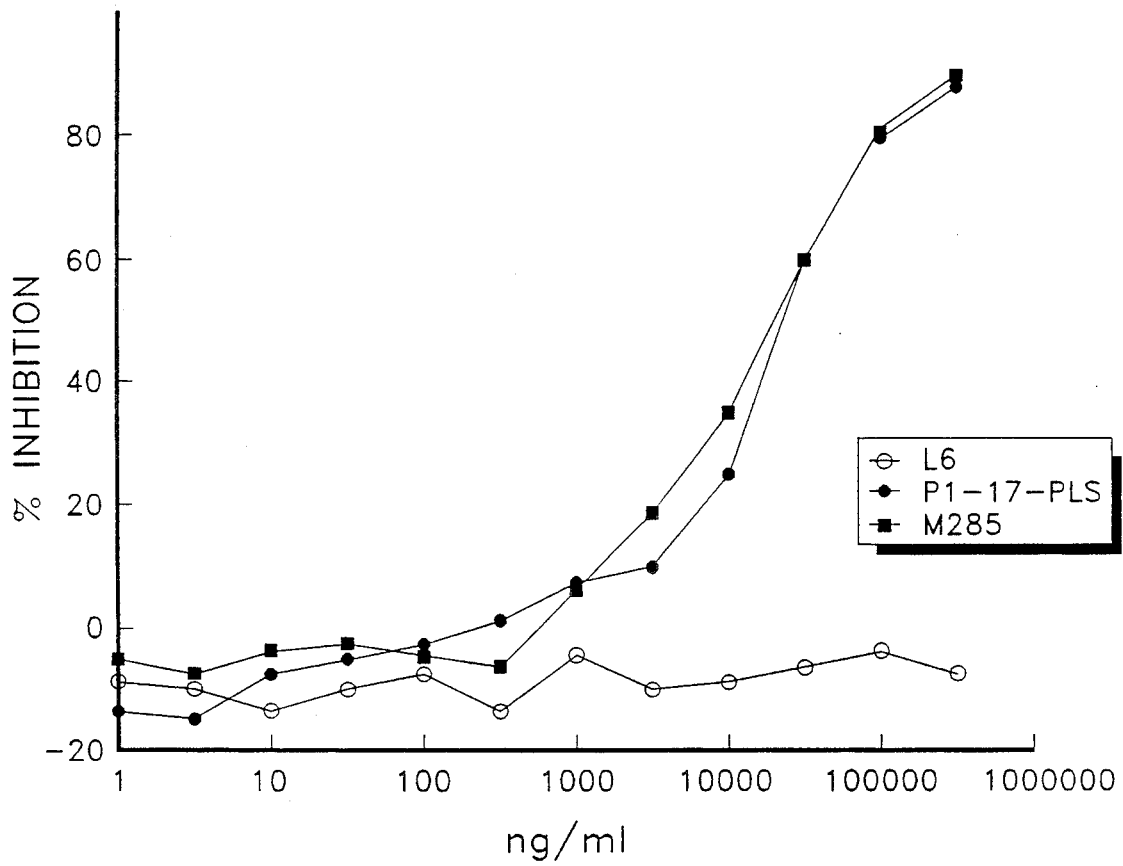
FIG. 8 is a graph of the competition binding assay of the L6-Poly-L-Lysine-Daunomycin (L6-PLS-ADM) conjugate to the fixed cell line 3347 (M285 designates the conjugate)

The binding of the immunoconjugate L6-PLS-ADM prepared as described above to tumor cells was tested. The binding was done using a competition assay in which different amounts of both native and conjugated L6 antibody were incubated with the tumor (metastatic colon carcinoma) cell line 3347 (Oncogen, Seattle, Wash.) and displaced using 10 ng of a fluorescent derivative (fluorescein isothiocyanate (FITC)) of L6 (FITC-L6). The level of inhibition of binding was compared as a function of the amount of introduced "cold" antibody. The immunoconjugate and the native L6 antibody produced the same binding curve. A conjugate to a nonspecific antibody (Igza), P1.17, (ATCC No. TIB10) showed no binding. These data are shown in FIG. 8.

Cytotoxicity of the L6-PLS-ADM immunoconjugate

Figure 9:
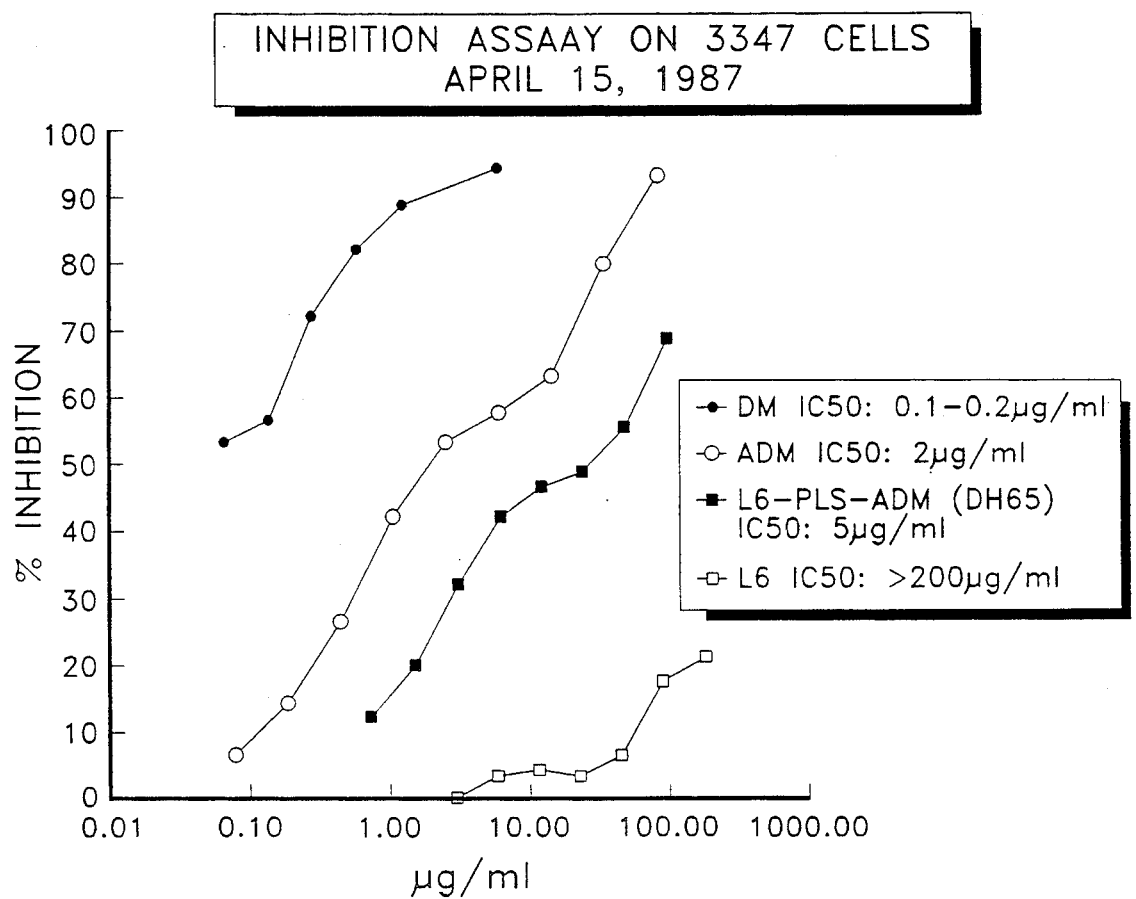
FIG. 9 is a graph of thymidine inhibition of the L6-PLS-ADM conjugate.
Figure 10:
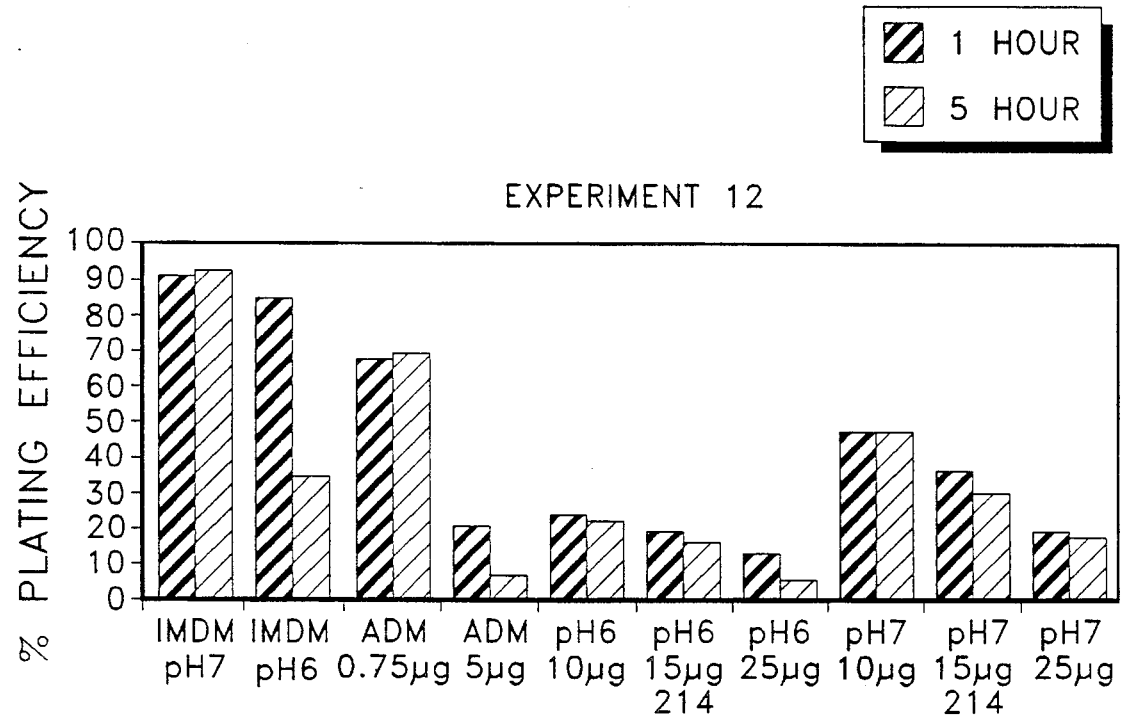
FIG. 10 is a graph of colony inhibition showing toxicity of the L6-PLS-ADM conjugate at pH 6 and pH 7 (M214 designates the conjugate)

The L6-PLS-ADM immunoconjugate was tested for its potential to inhibit growth of tumor cells. Two inhibition assays were used: 1) $^3$[H] Thymidine, and 2) colony assay. Both assays correlated well. These results are summarized in FIGS. 9 and 10. The immunoconjugate was toxic even at pH 7-7.5, with an inhibition constant of 5 μg/ml (based on drug concentration). The conjugate was less toxic, however, than free drugs: DM (at 0.2 μg/ml) and ADM (at 2 μg/ml). When the conjugate was exposed to low pH (pH 6) the toxicity was 15-25% higher than in neutral pH and was similar to the free ADM toxicity. L6 antibody alone did not inhibit under these conditions.

EXAMPLE VI

Localization of the L6-PLS-ADM Immunoconjugate in vivo

The ability of L6-PLS-ADM conjugate prepared as described in Example V to localize in tumors, compared to unconjugated L6 monoclonal antibody, was examined in nude mice bearing human tumor xenografts. Two randomized groups of 19 mice each were used. Each mouse bore 2 L6 antigen-positive bilateral subcutaneous human metastatic lung carcinoma tumors (H2981) (Oncogen, Seattle, Wash.) of approximately 7×7 mm at the start of the experiment. The viability of the tumors was determined by observing enlargement of each tumor for two weeks following implantation.

$^{125}$I was used to label the specific L6 antibody by the chloramine T method described by Beaumier et al, *J. Nuc. Med.*, 27, P. 824 (1986). Each mouse received approximately 5 μCi of L6 antibody (specific activity approximately 10 μCi/μg) along with either 50 μg L6 or 50 μg unlabelled L6-PLS-ADM conjugate. In addition, each mouse also received a comparable $^{131}$I-labelled non-specific monoclonal antibody (IF5) (Oncogen, Seattle Wash.) of the same subclass (IgG2a) described by Clark et al, PNAS, 83 p. 4494 (1986), along with 50 μg of unlabelled IF5 antibody, coadministered i.v.

At selected time points, (6, 24, 48, 72, and 120 hours), 4 animals from each group were anesthesized, exsanguinated through the orbital plexus and sacrificed. Selected tissues, tumor, blood, liver, spleen and kidney were removed, weighed and counted in a gamma counter capable of differentiating between $^{125}$I and $^{131}$I.

Figure 11:
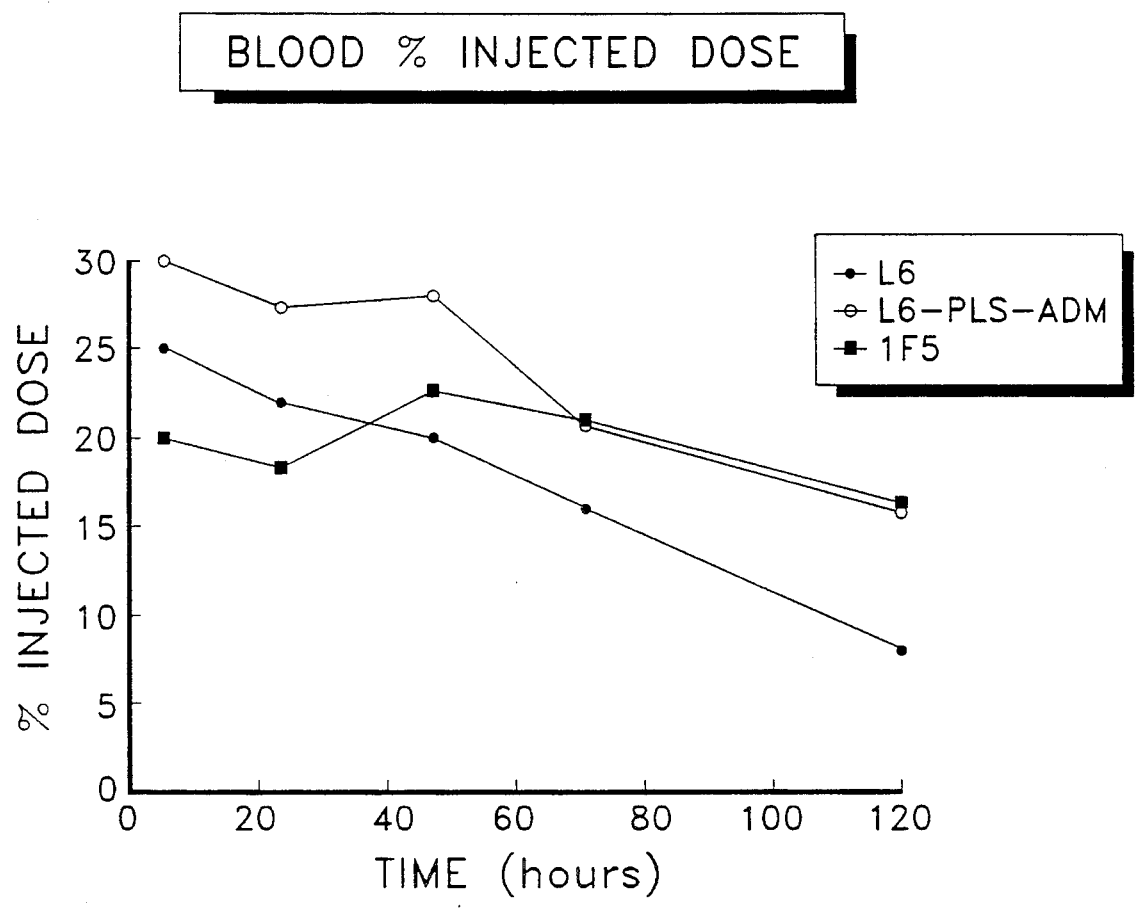
FIG. 11 is a graph showing the blood clearance of the L6-PLS-ADM conjugate in nude mice. This graph compares the blood clearance of the conjugate to native L6 antibody and to the non-specific antibody IF5.

Blood clearance was slower with the L6-PLS-ADM conjugate compared to either L6 or IF5 antibody, as seen in FIG. 11. This was probably caused by the increased size of the L6-PLS-ADM conjugate.

Figure 12:
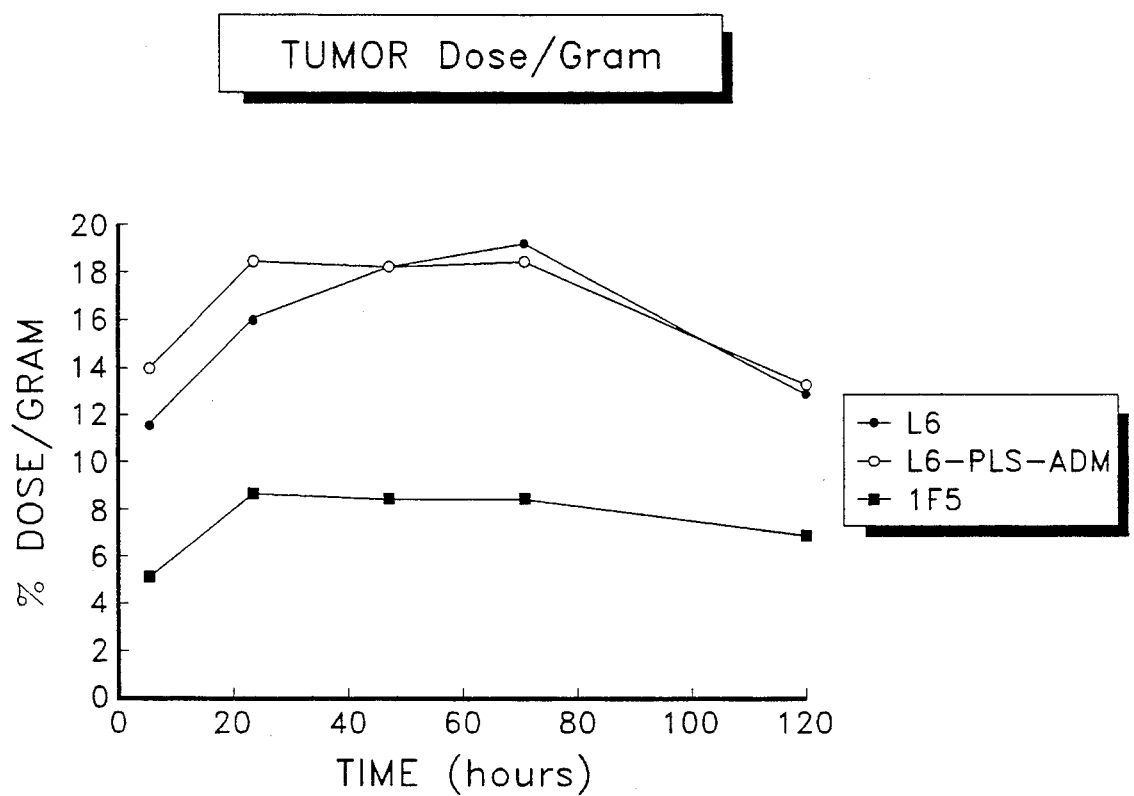
FIG. 12 is a graph of the in vivo tumor uptake of L6-PLS-ADM conjugate, L6 antibody alone and the non-specific IF5 antibody.
Figure 13:
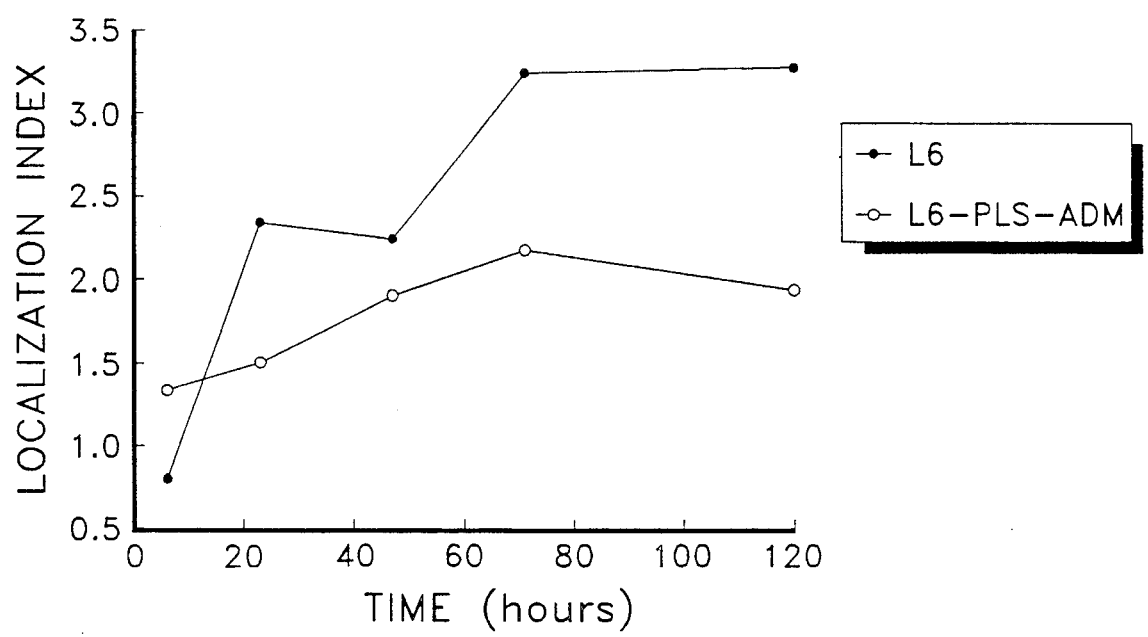
FIG. 13 is a graph of the localization index (L.I.) as a function of time for the L6-PLS-ADM conjugate and the native L6 antibody.
Figure 14:
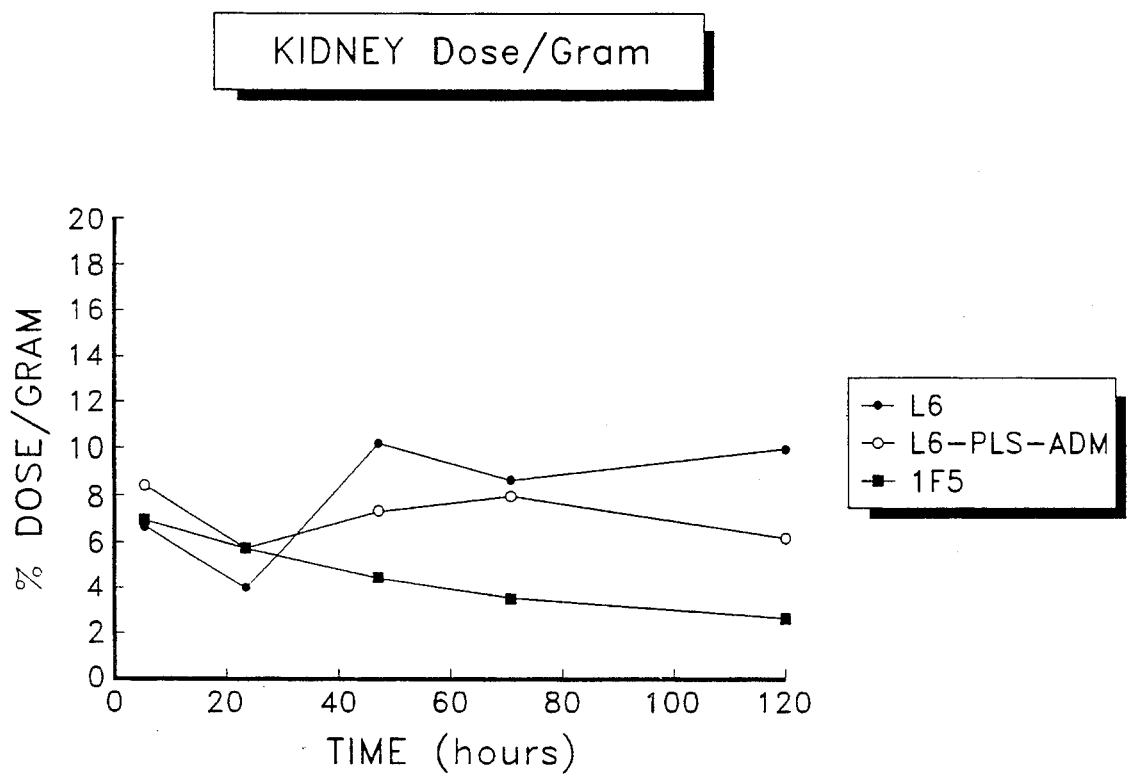
FIG. 14 is a graph of the in vivo kidney uptake of the L6-PLS-ADM conjugate, L6 antibody alone and the IF5 non-specific antibody.
Figure 15:
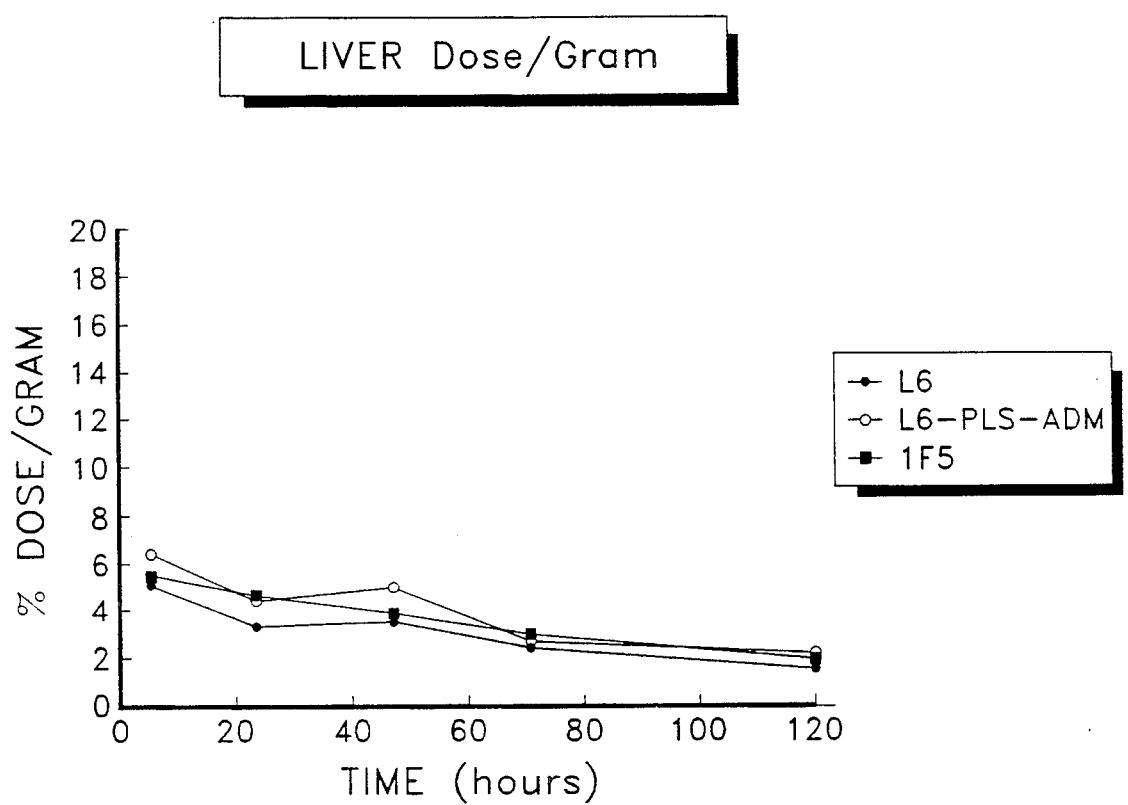
FIG. 15 is a graph of the in vivo liver uptake of the L6-PLS-ADM conjugate, L6 antibody alone and the IF5 non-specific antibody.

Most significantly, the tumor uptake was similar for both the L6 antibody and the L6-PLS-ADM conjugate, both of which were much higher than the uptake of non-specific IF5 antibody as shown in FIG. 12. The peak uptake was between 48 and 72 hrs. The localization index (L.I.) for the L6 antibody and the L6-PLS-ADM conjugate peaked at 72 hrs., with values of 3.3 and 2.2 respectively (FIG. 13). Uptake by normal tissue, kidneys and liver was comparable for all the preparations, as illustrated in FIGS. 14 and 15.

The examples presented above demonstrate that pH sensitive immunoconjugates for joining antibodies reactive with tumor associated antigens with chemotherapeutic agents may be formed according to the present invention and used to target tumor cells, without requiring that the immunoconjugates cross the tumor cell membrane. As shown by these examples, the immunoconjugates will be unstable within the range of pH of human tumor tissue (pH 4-6). While the examples demonstrate that up to 25 molecules of chemotherapeutic agent were bound per antibody molecule, higher ratios of drugs to antibody may be achieved using the procedures described herein, or by varying aspects of these procedures to maximize the association of chemotherapeutic agent with the antibody.

The immunoconjugates described herein have relatively little toxicity until they reach tumor tissue where, due to the low pH, the conjugates release the active chemotherapeutic agent which can then diffuse into tumor cells.

From the pH values for tumor tissue obtained in the above study, set forth in Table 1, the efficacy of the immunoconjugates described in this invention may depend on the level of chemotherapeutic agent releasable in the range of pH 6.0 to pH 6.7. In addition, since only a small percentage of an injected dose of immunoconjugate will reach the tumor vicinity (depending on the ability of the antibody to act as a carrier, i.e., to target the tumor site, which is a function of the antibody's affinity for the tumor-associated antigen with which it reacts) it is necessary to obtain conjugates with as many molecules of chemotherapeutic agent bound to an antibody molecule as possible, preferably 10 to 50 molecules of agent per molecule of antibody.

In addition, during nonequilibrium pH conditions in vivo in the tumor tissue region, portions of the agent may dissociate from the conjugate and be taken up by the tumor cells, so that higher amounts of chemotherapeutic agent will ultimately be released from the antibody leading to higher effective therapeutic levels of the drug at the tumor for a given dose of immunoconjugate. The ability of the immunoconjugates of the present invention to take advantage of the low pH occurring in tumor tissues in chemotherapy may be enhanced by further lowering the pH of such tissue, for example by intravenous infusion of large doses of glucose. Ashby, Lancet, Augost 6, pp. 312-313 (1966).

The above results demonstrate that the immunoconjugates of the present invention can localize in tumors in an animal model and may be useful for directing chemotherapeutic agents to tumors in humans for treatment.

The chemotherapeutic effectiveness of the immunoconjugates of the present invention may be determined experimentally, for example, by administering a range of doses of the immunoconjugates into tumor-bearing animal models. Effectiveness of the immunoconjugates may then be assessed by determining the extent of destruction of tumor cells. In addition, where tumors consist of mixed populations of antigen positive and antigen negative tumor cells, observations on the number of nonantigen bearing tumor cells (i.e., "antigen negative" cells) destroyed out of the total mixed population of tumor cells, can provide information on the number of antigen positive cells required to achieve chemotherapeutically effective levels of drug in tumor tissues using the immunoconjugates of the present invention. In addition, the immunoconjugates may be radiolabeled using standard procedures for administration to humans, for example, to determine the dose per gram of immunoconjugate required to achieve a therapeutic effect.

While the present invention has been described in conjunction with preferred embodiments, one of the ordinary skill, after reading the foregoing specification, will be able to effect various changes, substitutions of equivalents, and alterations to the compositions and methods set forth herein. It is therefore intended that the protection granted by Letters Patent thereon be limited only by the appended claims and equivalents thereof.

The embodiments of the invention in which an exclusive property or privilege is claimed are defined as follows:

1. A process for producing a pH-sensitive immunoconjugate between an antibody reactive with a tumor-associated antigen and a chemotherapeutic agent comprising:
   a) attaching aconitic anhydride to an available amino group of a chemotherapeutic agent to form a first intermediate with a free carboxyl group;
   b) reacting said free carboxyl group of said first intermediate with the amino group of a lysine containing amino acid spacer molecule using a first activating reagent to form a chemotherapeutic agent-spacer-reagent compound;
   c) reacting said chemotherapeutic agent-spacer reagent compound with a second activating reagent to form modified chemotherapeutic agent-spacer-reagent compound;
   d) reacting the lysine group of an non-intervalizing antibody using a thiolating reagent to form modified antibody; and
   e) reacting said modified chemotherapeutic agent-spacer reagent compound with said modified antibody to form an immunoconjugate comprising a chemotherapeutic agent coupled by a spacer molecule to an antibody;
whereby said immunoconjugate dissociates in low pH tumor tissue, releasing said chemotherapeutic agent in said tumor tissue.

2. The process according to claim 1 wherein said spacer molecule is poly-L-Lysine.

3. The process according to claim 2 wherein said first activating agent used to form the chemotherapeutic agent-spacer-reagent compound is 1-ethyl-3-(dimethylaminopropyl)carbodiimide hydrochloride.

4. The process according to claim 2 wherein said second activating reagent is maleiimide reagent.

5. The process according to claim 4 wherein said maleiimide reagent is sulfosuccinimidyl-4-(N-maleimidomethyl)cyclohexane-1-carboxylate.

6. The process according to claim 2 wherein said thiolating reagent is S-acetylmercaptosuccinicanhydride.

7. The process according to claim 1, wherein said chemotherapeutic agent is selected from the group consisting of Daunomycin, Mitomycin C, Adriamycin and Methotrexate.

8. The process according to claim 7 wherein said chemotherapeutic agent is Daunomycin.

9. The process according to claim 7, wherein said antibody is L6 monoclonal antibody.

10. The process according to claim 7, wherein said antibody is an antibody which is not internalized by tumor cells.

* * * * *